(12) United States Patent
Katz et al.

(10) Patent No.: US 9,266,915 B2
(45) Date of Patent: *Feb. 23, 2016

(54) SYNTHESIS OF OPEN METAL CARBONYL CLUSTERS

(71) Applicants: Chevron U.S.A. Inc., San Ramon, CA (US); The Regents of the University of California, Oakland, CA (US)

(72) Inventors: Alexander S. Katz, Richmond, CA (US); Alexander Kuperman, Richmond, CA (US); Alexander Okrut, San Francisco, CA (US); Ron C. Runnebaum, Sacramento, CA (US); Xiaoying Ouyang, El Cerrito, CA (US)

(73) Assignees: Chevron U.S.A. Inc., San Ramon, CA (US); The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/731,082

(22) Filed: Jun. 4, 2015

(65) Prior Publication Data

US 2015/0266912 A1 Sep. 24, 2015

Related U.S. Application Data

(63) Continuation of application No. 14/034,406, filed on Sep. 23, 2013.

(60) Provisional application No. 61/705,062, filed on Sep. 24, 2012.

(51) Int. Cl.
*C07F 15/00* (2006.01)
*B01J 31/24* (2006.01)
(Continued)

(52) U.S. Cl.
CPC ............ *C07F 15/0033* (2013.01); *B01J 31/066* (2013.01); *B01J 31/1616* (2013.01); *B01J 31/1683* (2013.01); *B01J 31/20* (2013.01); *B01J 31/24* (2013.01); *B01J 31/2404* (2013.01);
(Continued)

(58) Field of Classification Search
CPC ....... C07F 15/004; B01J 31/24; C01G 55/008
USPC .............. 585/277; 556/16; 423/418; 502/161
See application file for complete search history.

(56) References Cited

U.S. PATENT DOCUMENTS 4,473,505 A  9/1984 Mitchell, III

FOREIGN PATENT DOCUMENTS

WO  2011/050300 A1  4/2011
WO  2011/057109 A1  5/2011

OTHER PUBLICATIONS

Adams et al., Organometallics, vol. 2, pp. 1257-1258 (1983).*

(Continued)

*Primary Examiner* — Porfirio Nazario Gonzalez
(74) *Attorney, Agent, or Firm* — E. Joseph Gess; Melissa M. Hayworth

(57) ABSTRACT

The present invention is directed to the synthesis of novel stable open metal clusters by selective oxidation of bound ligands. The synthesis comprises, for example, using an amine based oxidant for decarbonylation of specific carbonyl ligands. The synthesis can also comprise further removal of a bound amine group by an acid. The resulting metal cluster contains a coordinatively unsaturated site comprising a carbonyl vacancy. The resulting metal cluster can be used as a catalyst in a variety of chemical transformations.

22 Claims, 10 Drawing Sheets

(51) Int. Cl.
| | |
|---|---|
| C01G 55/00 | (2006.01) |
| B01J 31/06 | (2006.01) |
| B01J 31/16 | (2006.01) |
| B01J 31/20 | (2006.01) |
| B01J 37/08 | (2006.01) |
| B01J 37/12 | (2006.01) |
| C07C 5/03 | (2006.01) |

(52) U.S. Cl.
CPC .......... *B01J37/08* (2013.01); *B01J 37/12* (2013.01); *C01G 55/008* (2013.01); *C07C 5/03* (2013.01); *C07F 15/004* (2013.01); *B01J 31/2457* (2013.01); *B01J 2231/645* (2013.01); *B01J 2531/0211* (2013.01); *B01J 2531/0288* (2013.01); *B01J 2531/827* (2013.01); *C07C 2531/24* (2013.01)

(56) References Cited

OTHER PUBLICATIONS

Tunik et al., Journal of Organometallic Chemistry, vol. 479, pp. 59-72 (1994).*

International Search Report and Written Opinion from corresponding International Application PCT/US2013/061476, mailed Jan. 22, 2014.

Richard D. Adams, et al., "Synthesis of open metal carbonyl cluster compounds. The reactions of closo-sulfido metal carbonyl cluster compounds with hydrogen sulfide. Synthesis and crystal and molecular structure of H2OS5(CO)14 (u3-S)2", Organomettallics, vol. 2, pp. 1257-1258 (1983).

Shih-Huang Huang et al., "Directed Synthesis of the Triangular Mixed-Metal Cluster H2RhRe2Cp(CO)9: Ligand Fluxionality and Facile Cluster Fragmentation in the Presence of CO, Halogenated Solvents, and Thiols", Organometallics, vol. 29, pp. 61-75 (2010).

Richard H. Hooker et al., "Photochemistry of Some Group 6A and 8 Metal-Metal Bonded Cyclopentadienylcarbonyl Dimers in Poly(vinyl) Films at 12-298 K", J. Chem. Soc. Dalton Trans., 1990(4), pp. 1221-1229 (1990).

Parish et al., "Organosilicon Chemistry. Part 24. Homogeneous Rhodium-catalysed Hydrosilation of Alkenes and Alkynes: The Role of Oxygen or Hydroperoxides", J C S Salton 1980, pp. 308-313.

Maitlis et al., "(Pentamethylcylcopentadienyl-Rhodium and -Iridium Complexes Part 35_Hydrogenation Catalysts Based on [(RhC5Me5)2(OH)3] and The Border Between Homogeneous and Heterogeneous Systems", J Mol. Cat. 1982, pp. 15,337-347.

James and Memon, "Kinetic study of iridium (I) complexes as homogeneous hydrogenation catalysts", Can J. Chem. 1968 (46) pp. 217-223.

S. P. Tunik et al., "Synthesis and structural characterization of the isomers of Rh6(CO)14L2 clusters (L=NCMe, Py, P(OPh)3), X-ray crystal structure of trans-Rh6(CO014{P(OPh3)}2", Journal of Organometallic Chemistry, 1994, vol. 479, pp. 59-72.

J.-M. Ha et al., "Synthesis and Characterization of Accessible Metal Surfaces in Calixarene-Bound Gold Nanoparticles", Langmuir, 2009, vol. 25, No. 18, pp. 10548-10553.

A. Okrut et al., "Stabilization of coordinatively unsaturated Ir4 clusters with bulky ligands: a comparative study of chemical and mechanical effects", Dalton Trans., 2012, vol. 41, pp. 2091-2099.

M. Shekhar et al., "Size and Support Effects for the Water-Gas Shift Catalysis over Gold Nanoparicles Supported on Model Al2O3 and TiO2" Journal of the American Chemical Society, 2012, vol. 134, pp. 4700-4708.

N. De Silva et al., "Patterned metal polyhedra using calixarenes as organizational scaffolds: Ir4-based cluster assemblies", Dalton Trans., 2010, vol. 39, pp. 2194-2197.

P. Chini et al., "New Tetrahedral Cluster Compounds of Iridium. Synthesis of the Anions [Ir4(CO)11X]- (X=Cl, Br, I, CN, SCN) and X-Ray Structure of [PPh4] [Ir4(CO)11Br]", Journal of Organometallic Chemistry, 1978, vol. 152, pp. C35-C38.

W. D. Williams et al., "Metallic Corner Atoms in Gold Clusters Supported on Rutile Are the Dominant Active Site during Water-Gas Shift Catalysis", Journal of the American Chemical Society, 2010, vol. 132, pp. 14018-14020.

B. R. James et al., "Kinetic study of indium(I) complexes as homogeneous hydrogenation catalysts1" Canadian Journal of Chemistry, 1968, vol. 46, pp. 217-223.

J. E. Hamlin et al., "Pentamethylcyclopentadienyl-Rhodium and -Iridium Complexes Part 35. Hydrogenation Catalysts Based on [(RhC5Me5)2(OH)3] and the Border Between Homogeneous and Heterogeneous Systems", Journal of Molecular Catalysis, 1982, vol. 15, pp. 337-347.

H. M. Dickers et al., "Organosilicon Chemistry. Part 24. Homogeneous Rhodium-catalysed Hydrosilation of Alkenes and Alkynes: The Role of Oxygen or Hydro-peroxides", J. C. S. Dalton, 1980, pp. 308-313.

R. Ros et al., "Chemistry of Tetrairidium Carbonyl Clusters. Part 1. Synthesis, Chemical Characterization, and Nuclear Magnetic Resonance Study of Mono-and Di-substituted Phosphine Derivatives. X-Ray Crystal Structure Determination of the Diaxial Isomer of [Ir4(CO)7(μ-CO)3(Me2PCH2CH2PMe2)]", J. Chem. Soc., Dalton Trans., 1986, pp. 2411-2421.

N. De Silva et al., "A bioinspired approach for controlling accessibility in calix[4]arene-bound metal cluster catalysts", Nature Chemistry, 2010, vol. 2, pp. 1062-1068.

Darensbourg, Donald J., et al., "Water-Soluble Organometallic Compounds. Synthesis, Spectral Properties, and Crystal Structure of 1,3,5-Triaza-7-phosphaadamantane (PTA) Derivatives of Metal Carbonyl Clusters: Ru3 (CO)9 (PTA)3 and Ir4(CO)7(PTA)5", Jr. Cluster Sci., 2000, vol. 11, No. 1.

L. Huang and Y. Xu, "SiO2-supported bimetallic Rh-Co catalysts derived from [Rh(CO)2CI]2 and cobalt carbonyls", Catalysis Letters, 1998, vol. 53, No. 3/04, pp. 177-183.

Supplementary European Search Report issued in corresponding EP Application No. 13838596.8 on Sep. 25, 2015.

* cited by examiner

SYNTHESIS OF OPEN METAL CARBONYL CLUSTERS

CROSS-REFERENCE TO RELATED APPLICATIONS

This application is a continuation of U.S. patent application Ser. No. 14/034,406 filed Sep. 23, 2013, entitled "Synthesis and Characterization of Open Metal Clusters" which claims priority from U.S. Provisional Patent Application No. 61/705,062, filed on Sep. 24, 2012, entitled "Synthesis of Open Metal Carbonyl Clusters", the contents of which are herein incorporated by reference in their entirety.

BACKGROUND OF THE INVENTION

1. Field of the Invention

Provided are open metal carbonyl clusters and a method for synthesizing the open metal carbonyl clusters. More specifically, provided is the synthesis of open Ir4 carbonyl clusters carrying phosphine ligands by selective oxidation using an oxidant. The open metal clusters are useful as reagents in a variety of chemical transformations.

2. Description of the Related Art

Increasing catalytic activity, particularly for hydrogenation catalysts, is always a valued goal. There are reports of oxidative activation of catalyst sites for homogeneous cationic complexes used in hydrosilylation. See, *Organosilicon Chemistry. Part 24. Homogeneous Rhodium-catalysed Hydrosilation of Alkenes and Alkynes: The Role of Oxygen or Hydroperoxides* by Parish et al. in *J C S Dalton* 1980, 308-313) and hydrogenation reactions (*Pentamethylcylcopentadienyl-Rhodium and-Iridium Complexes Part 35__Hydrogenation Catalysts Based on* $[(RhC_5Me_5)_2(OH)_3]$ *And The Border Between Homogeneous and Heterogeneous Systems* by Maitlis et al. in *J Mol. Cat.* 1982, 15, 337-347. These studies are preceded by reports of increased hydrogenation activity after oxygen treatment; for instance, a 100-fold increase in hydrogenation activity of maleic acid is observed upon treating the homogeneous trans-$IrX(CO)(PPh_3)_2$, where X=Cl, Br complex with small amounts of oxygen (*Kinetic study of iridium (I) complexes as homogeneous hydrogenation catalysts* by James and Memon in *Can J. Chem.* 1968, 46:217-223). Both the Parish et al. and Maitlis et al. manuscript attribute the role of oxygen treatment as one that removes ligands (e.g., oxidizes triphenylphosphine to triphenylphosphine oxide), thereby creating a coordinatively unsaturated center that is catalytically active. The Maitlis et al. article articulates how such species are unstable and readily aggregate into larger particles in general.

Open metal carbonyl clusters are known, as are various syntheses therefore. For example, "Stabilization of coordinatively unsaturated $Ir_4$ clusters with bulky ligands: a comparative study of chemical and mechanical effects", by Alexander Okrut et al., *Dalton Trans.*, (2012) 41:2019, describes the synthesis of a metal carbonyl cluster that has open sites. The cluster is synthesized thermally and stabilized with calixarenes.

Trimethylamine oxide is used in the synthesis of ligand-substituted clusters, as shown in "Synthesis and structural characterization of the isomers of $Rh_6(CO)_{14}L_2$ clusters (L=NCMe, $P_4$, $P(OPh)_3$), X-ray crystal structure of trans-$Rh_6(CO)_{14}\{P(OPh)_3\}_2$", by Tunik et al. *Journal of Organometallic Chemistry*, (1994) 479:59-72.

The use of a brominating agent in the synthesis of ligand-substituted clusters is described in "New Tetrahedral Cluster Compounds of Iridium. Synthesis of the Anions $[IR_4(CO)_{11}X]^-$ (X=Cl, Br, I, Cn, SCN) and X-ray structure of $[PPh_4][Ir_4(CO)_{11}Br]$", Chini et al., *Journal of Organometallic Chemistry*, (1978) 152:C35-C38. See also "Chemistry of Tetrairidium Carbonyl Clusters. Part 1. Synthesis, Chemical Characterization, and Nuclear Magnetic Resonance Study of Mono- and Di-substituted Phosphine Derivatives. X-Ray Crystal Structure Determination of the Diaxial Isomer of $[Ir_4(CO)_7(\mu\text{-}CO)_3(Me_2PCH_2CH_2PMe_2)]$", Ros et al., *J. Chem. Soc., Dalton Trans.* (1986); and "Patterned metal polyhedra using calixarenes as organizational scaffolds: $Ir_4$-based cluster assemblies", de Silva et al., *Dalton Trans.*, (2010) 39:2194-2197.

The synthesis of an open gold cluster has open sites and is stabilized with calixarene ligands is described in "A bioinspired approach for controlling accessibility in calyx [4]arene-bound metal cluster catalysts", by de Silva et al., *Nature Chemistry*, (2010) 2:1062-1068.

The synthesis of an open gold nanoparticles that has open sites and is stabilized with calixarene ligands is described in "Synthesis and Characterization of Accessible Metal Surfaces in Calixarene-Bound Gold Nanoparticles", by Jeong-Myeong Ita et al., *Langmuir*, (2009) 25(18):10548-10553.

An objective of the present invention is to provide a simple and efficient synthesis for an open metal carbonyl cluster, which open cluster is useful as a catalyst, is stable, and demonstrates improved catalytic activity.

SUMMARY OF THE INVENTION

Provided is a synthesis for an open metal carbonyl cluster comprising a chemical reaction between an opening reagent and a closed metal carbonyl cluster. More specifically, the stable open metal carbonyl clusters are prepared by selective oxidation using an oxidant, such as trimethylamine oxide. The opening agent or oxidant reacts with a bound carbonyl group (or groups) so as to unbind it from the cluster and leave behind a CO-labile ligand on the cluster. Upon treating the open cluster with CO, the CO-labile ligand is readily removed and the cluster is recarbonylated. Thus, the resulting cluster is stable but can be easily recarbonylated.

The open metal carbonyl cluster involves having one or more carbonyls on the cluster missing. The sites formerly held by the missing carbonyls can be either occupied with a CO-labile ligand, such as a tertiary amine, or is simply a coordinately unsaturated site which is a CO vacancy. In one embodiment, the metal carbonyl cluster is an open $Ir_4$ carbonyl cluster bound with three calixarene phosphine ligands for steric protection against aggregation.

Among other factors, it has been found that an open metal carbonyl cluster can be prepared by means of a chemical reaction between an opening reagent and closed metal carbonyl cluster, without the need for a thermal supported reaction. In particular, the present process permits the selective oxidation of bound CO ligands to $CO_2$, using a selective oxidant. The selective oxidant in one embodiment is trimethylamine oxide. The open metal clusters are free of aggregation by employing calixarene phosphine ligands for steric protection. The resulting open metal clusters have a coordinately unsaturated site comprising a carbonyl vacancy that acts as a highly active catalyst site. These sites are useful in catalysis and render the open metal carbonyl cluster an effective catalyst. Furthermore, upon treating the open metal carbonyl cluster with oxygen, the catalytic activity of compound is greatly enhanced.

DETAILED DESCRIPTION OF THE INVENTION

Figure 1:
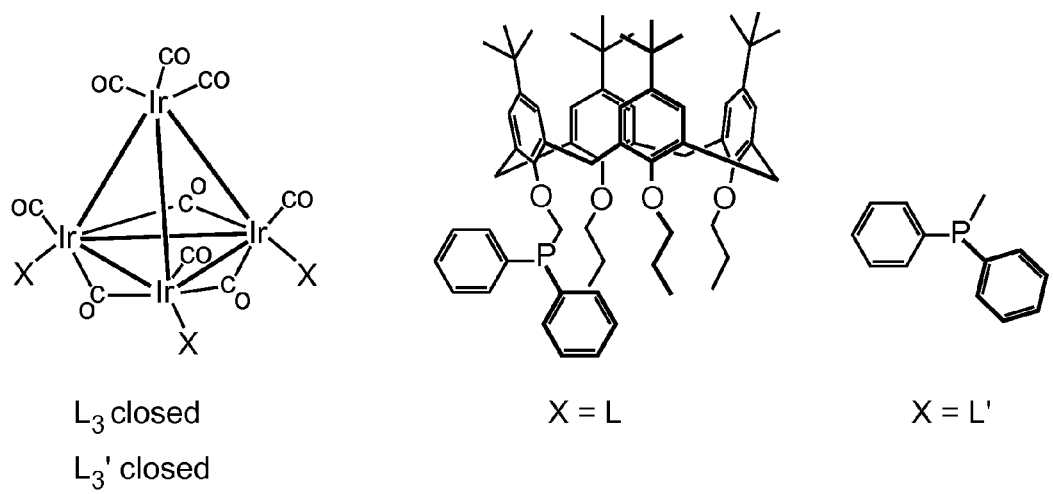
FIG. 1. Schematic illustration of trisubstituted $Ir_4$ carbonyl parent cluster having formula $Ir_4(CO)_9L_3$ and consisting of both bridging and terminal CO ligands (left-most panel); calixarene phosphine L ligand used in current work for synthesis of cluster $L_3$ closed (middle panel); and sterically less bulky ligand L' (right-most panel) used for synthesis of cluster $L_3'$ closed.

The present invention provides a general method for the synthesis of open metal carbonyl clusters, which in one embodiment are bound by with three calixarene phosphine ligands for steric protection against aggregation. Metal carbonyl clusters are clusters containing metal bonds to a bound carbonyl, which cluster can also contain other ligands such as phosphine, carbene, etc. The open metal clusters comprise either (i) easily CO-labile ligands, e.g., a tertiary amine ligand or (ii) a coordinatively unsaturated site consisting of a CO vacancy. The synthesis of the open site in both cases requires the selective oxidation of bound CO ligands to $CO_2$, using a selective oxidant such as trimethylamine oxide.

By an "open" metal cluster is meant for the purposes of the present invention having one or more carbonyls of the metal cluster missing. The sites formerly held by the missing carbonyls can be either occupied with a CO-labile ligand, such as trimethylamine, and/or having a vacant site altogether. A labile, or CO-labile, ligand for the present purposes is one that is readily removed upon treating the cluster with CO. Thus, for the present purposes, an open cluster is one where the site that used to be occupied with CO, before opening, is able to be readily recarbonylated and reoccupied upon treatment with CO. This can be done, for example, upon treating the cluster with CO gas at ambient conditions. If rebinding of the CO is not readily accomplished, the cluster is not considered open. Prior art clusters where the CO has been replaced with an anion such as Br are not open as the cluster is not recarbonylated upon treatment with a CO atmosphere. The anions, such as bromine, are strongly coordinated and are not readily replaced upon treatment with a CO atmosphere. See, for example, Williams et al., J. Am. Chem. Soc., 2010, 132 pages 14018-14020; and, Shekkar, et al., J. Am. Chem. Soc., 2012, 134, pages 4700-4708.

The "open" nature of the metal cluster has been found possible by using a selective oxidant to react with the closed cluster to create the open sites. CO-labile ligands besides trimethylamine oxide include compounds having a lone pair of electrons on oxygen such as ethers; amines; ammonia; dioxygen or nitrogen. In general, the CO-labile ligands can be any nitrogen-containing compound coordinating through a nitrogen or any oxygen-containing compound coordinating through an oxygen. As noted above, the open metal clusters of the present invention can be regenerated to the corresponding closed cluster by binding CO ligands to the open sites, e.g., upon treating the cluster with CO gas at ambient conditions.

In one embodiment, the metal carbonyl cluster is an open $Ir_4$ carbonyl cluster bound with three calixarene phosphine ligands for steric protection against aggregation. Calixarene related compounds and ligands are known and in general are useful for steric protection against aggregation. Such compounds and ligands are described, for example, in PCT/US10/55686, "Metal Colloids with Accessible Metal Surfaces", filed Nov. 5, 2010; and PCT/US10/53818, "Calixarene-Bound Iridium-Containing Metal Colloids", filed Oct. 22, 2010, with the subject matter of both applications being incorporated herein by reference in their entirety.

The example below demonstrates a present synthesis of an open $Ir_4$ carbonyl cluster that is bound with three calixarene phosphine ligands and an easily CO-labile trimethyl amine ligand at the open site, which used to be occupied by the strongly binding ligand CO. As a comparison of the two clusters L and L' as defined in FIG. 1 shows, a sterically bulky calixarene phosphine ligand is important for preserving the stability of the ensuing open cluster. When the ligand is replaced with a smaller, less sterically demanding diphenylmethylphosphine ($PPh_2Me$), for example, cluster aggregation can ensue upon synthesizing an open cluster.

Figure 2:
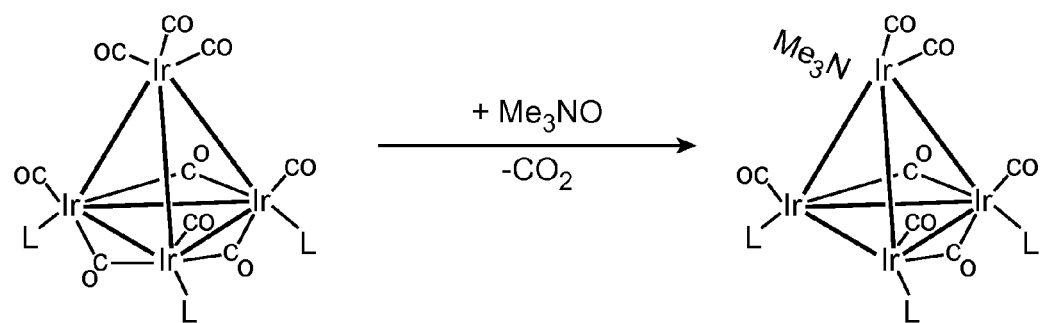
FIG. 2. Schematic drawing of the chemical decarbonylation of $L_3$ (left) to $L_3$ open with amine (right).

The synthesis of an open cluster is schematically represented in FIG. 2, starting with the parent $L_3$ closed cluster shown in FIG. 1. An example of a typical synthesis procedure follows. 100 μL of a 0.13 mM solution of $Me_3NO$ in dichloromethane (corresponds to 0.13 mmol $Me_3NO$) were added to a solution of $Ir_4(CO)_9$[t-butyl-calix[4]arene$(OPr)_3$ $(OCH_2PPh_2)$] ($L_3$) (51 mg, 0.013 mmol, in 3 ml decane). The mixture was stirred for 1 hour.

Figure 3:
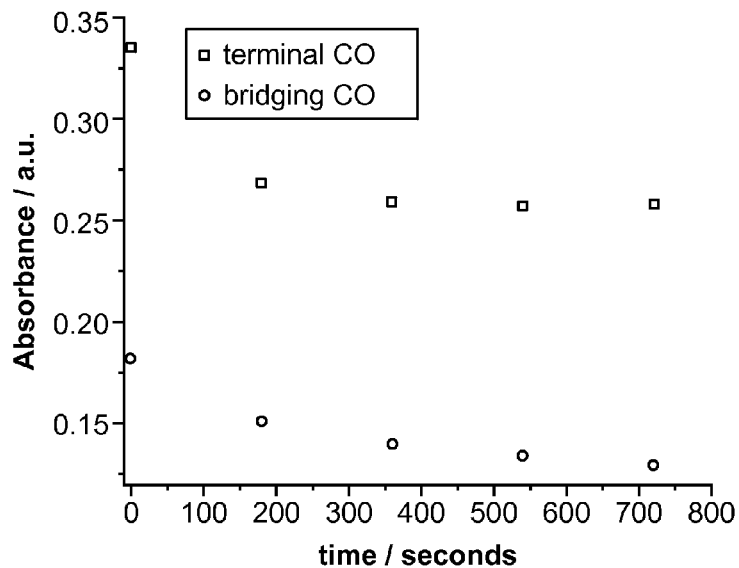
FIG. 3 shows intensity decay during decarbonylation for selected peaks corresponding to terminal (1988 $cm^{-1}$) and bridging (1787 $cm^{-1}$) CO bands FIG. 4. $^1$H NMR spectra for $L_3$ closed (bottom); $L_3$ open with amine, corresponding to after decarbonylation (middle); and recarbonylated $L_3$ open with amine, corresponding to after CO exposure of the decarbonylated cluster (top).

Decarbonylation was accompanied by an immediate change in color of the solution containing the cluster from initial yellow (corresponding to the parent $L_3$ closed cluster in FIG. 1) to brown. The decarbonylation process could be followed using in-situ (time-resolved) FTIR spectroscopy as shown in FIG. 3 for 1787 $cm^{-1}$ (bridging) and 1988 $cm^{-1}$ (terminal). This data shows the decarbonylation to be complete in approximately 10 min, and to result in loss of both terminal and bridging CO ligands. There appears to be a more significant decrease in the bridging versus terminal CO band intensity. This trend is paralleled for data in the integrated CO band intensity for the bridging and terminal regions. The fully integrated CO band intensity drops from 100% to about 93% for terminal CO and to 73% for bridging CO during decarbonylation.

Figure 4:
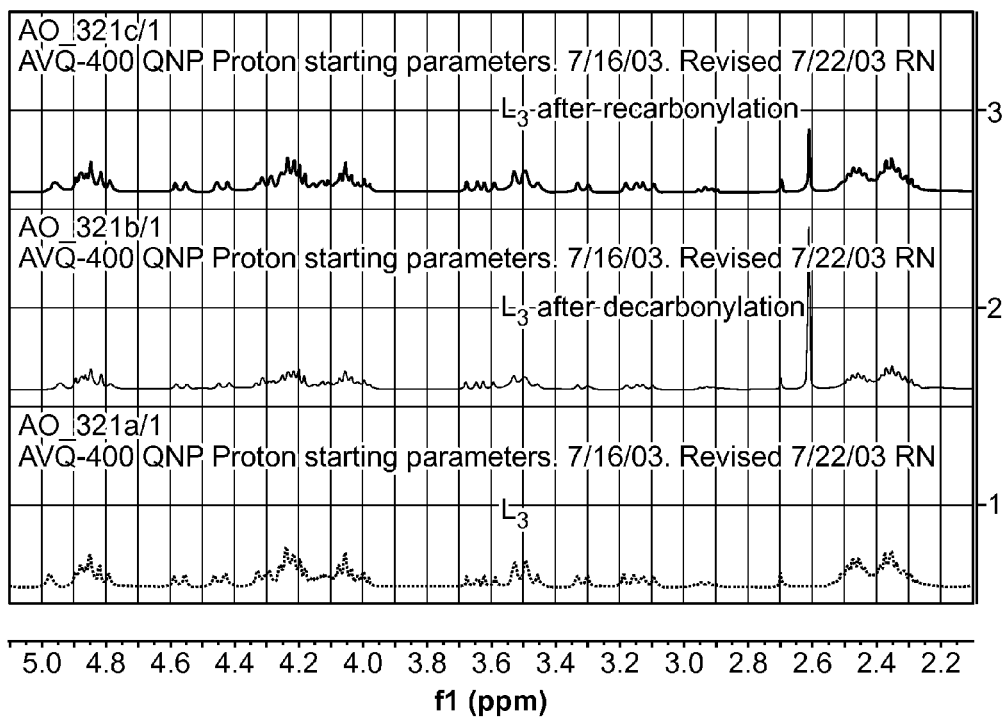

The synthesis of $L_3$ cluster open with amine ligands shown in FIG. 2 was also followed via NMR spectroscopy, by performing the decarbonylation as stated above except using deuterated decane-d14 as solvent. FIG. 4 shows the $^1H$ NMR spectra both before and after addition of $Me_3NO$. The appearance of a singlet peak at 2.6 ppm with a relative intensity corresponding to ~9H indicates the presence of coordinated $Me_3N$ as ligand. $^{31}P$ NMR spectra do before and after addition of $Me_3NO$ appear unchanged, and, importantly, do not show any evidence of phosphine ligand oxidation (i.e. no phosphine oxide resonances as would be expected in the vicinity of 23 ppm).

Next, the decarbonylated cluster $L_3$ open with amine ligand (right) in FIG. 2 was recarbonylated, in order to assess the accessibility and stability of the open cluster, in a decane solution at room temperature. This was performed as follows: A solution of the $L_3$ cluster open with amine ligand (51 mg [0.013 mmol] in 3 ml decane) was exposed to a CO gas atmosphere (1.2 atm) for a period of 1 hour. During that time, there was a visual color change of the solution from the brown color characteristic of $L_3$ cluster open with amine ligand to a yellow color reminiscent of the parent $L_3$ closed cluster.

Figure 6:
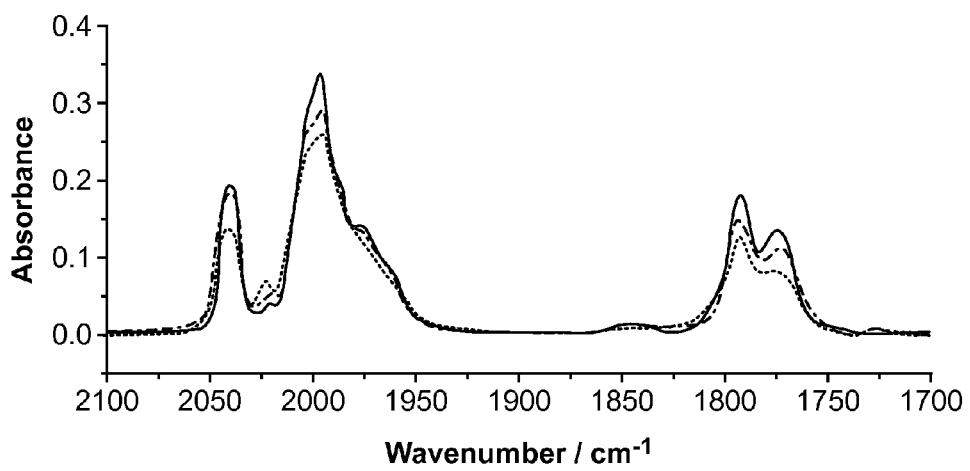
FIG. 6. FTIR spectra of $L_3$ (black), $L_3$ after decarbonylation (red, dotted) and $L_3$ after recarbonylation (dash-dotted).

The degree of recarbonylation in solution can be quantitatively assessed in order to provide direct evidence of the stability of the open clusters in decane solution at room temperature, since only stable clusters are anticipated to be accessible for recarbonylation. After exposure to of the $L_3$ cluster open with amine ligand to a CO atmosphere, FTIR spectra were recorded and compared to spectra of both $L_3$ closed as well as $L_3$ cluster open with amine ligand. These spectra are shown in FIG. 6. The total integrated intensity for terminal and bridging CO bands increased from values quoted above for $L_3$ cluster open with amine ligand to values corresponding to 96% (for terminal) and 86% (for bridging) of the integrated CO band intensity present in $L_3$ closed. The similarity of the integrated CO band intensity between recarbonylated and $L_3$ closed strongly suggests stability of the $L_3$ open with amine cluster in decane solution at room temperature.

Figure 5:
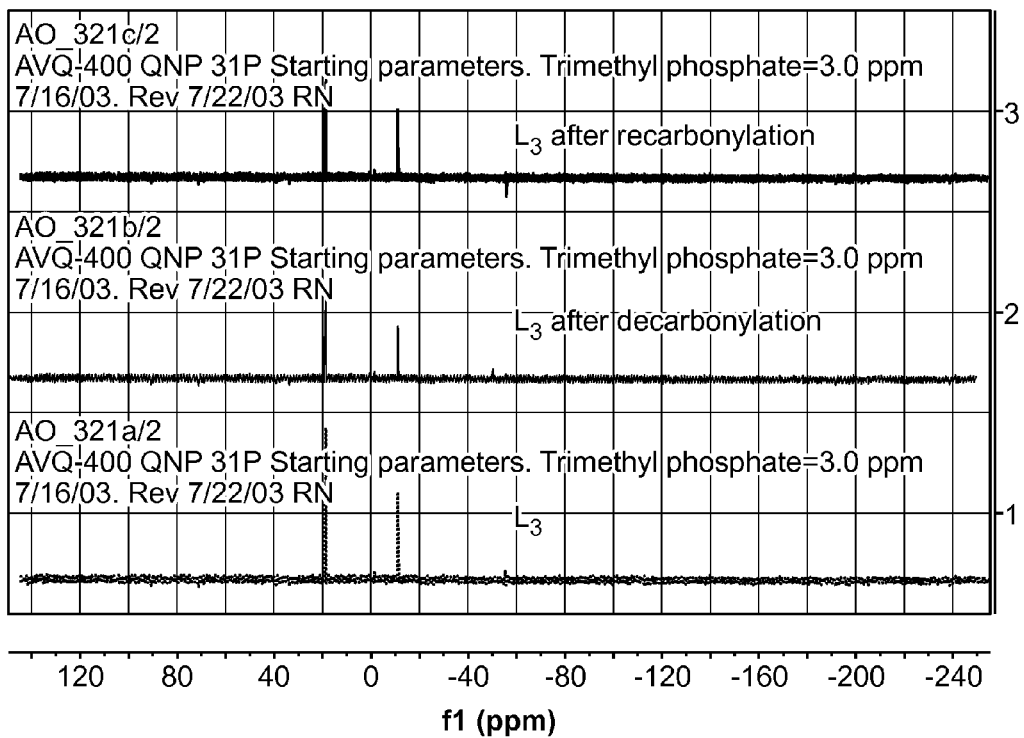
FIG. 5. $^{31}$P NMR spectra for $L_3$ closed (bottom); $L_3$ open with amine, corresponding to after decarbonylation (middle); and recarbonylated $L_3$ open with amine, corresponding to after CO exposure of the decarbonylated cluster (top).

The integrity of the cluster following recarbonylation can also be followed via NMR spectroscopy. The $^1H$ NMR spectrum of the recarbonylated cluster in FIG. 4 shows a partial decrease in the bound trimethylamine resonance corresponding to 25% of its value in $L_3$ cluster open with amine ligand. This suggests that some bound amine remains, likely due to equilibrium limitations in the closed system used for recarbonylation. No change in the $^{31}P$ NMR spectrum was observed after recarbonylation, as shown in FIG. 5.

Figure 7:
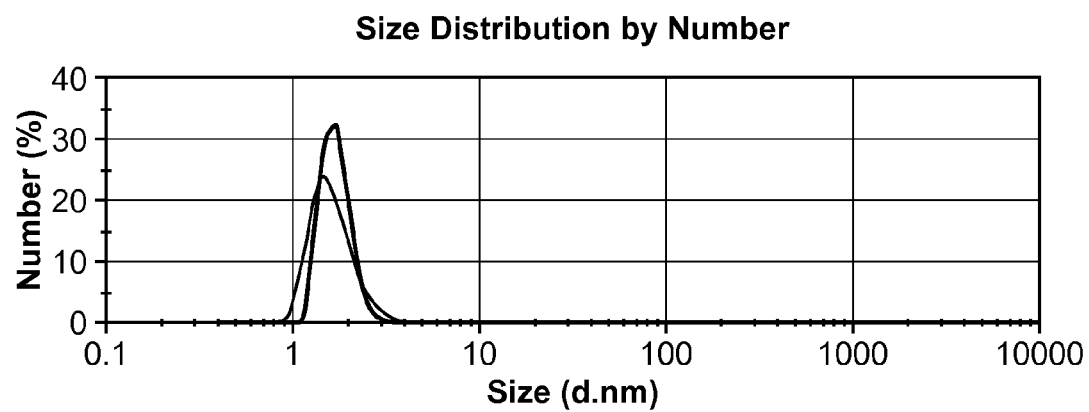
FIG. 7. DLS data of $L_3$ closed and $L_3$ open with amine.

The data above suggests a lack of cluster aggregation during decarbonylation as well as recarbonylation, especially the FTIR data in FIG. 6 showing the similarity of the original bands and bands in the recarbonylated cluster, as discussed above. Further direct confirmation of cluster stability was assessed using dynamic light scattering (DLS). DLS data for $L_3$ closed and $L_3$ cluster open with amine ligand is shown in FIG. 7. This data unequivocally demonstrates that there is no cluster aggregation accompanying decarbonylation, as the particle size remains virtually unchanged for clusters consisting of $L_3$ closed and $L_3$ cluster open with amine ligand. This result is drastically different, as significant aggregation is observed, when the sterically bulky calixarene phosphine consisting of ligand L shown in FIG. 1 is replaced with a smaller phosphine consisting of ligand L' in FIG. 1.

Figure 8:
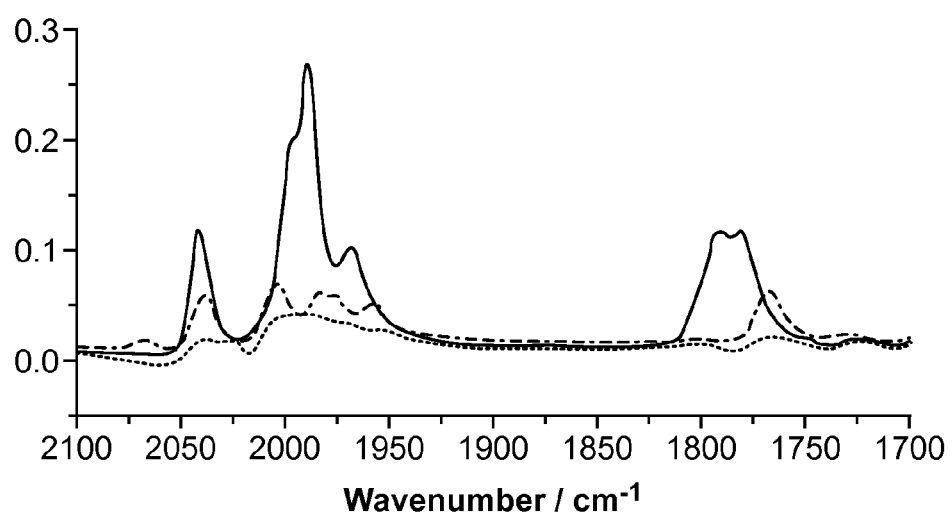
FIG. 8. FTIR spectra of $L'_3$ closed, $L'_3$ closed after decarbonylation (dotted) and $L'_3$ after recarbonylation (dash-dotted).
Figure 9:
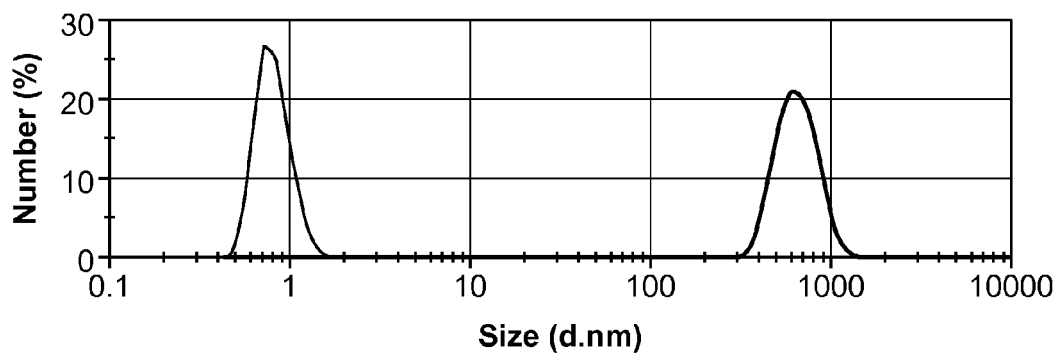
FIG. 9. DLS data of $L'_3$ closed before decarbonylation and L3' closed after treatment with trimethylamine oxide.

When treating a decane solution of cluster $L_3$' closed with $Me_3NO$ in a similar manner as described above for $L_3$ closed, a yellow-brownish precipitate forms from the initially transparent yellow decane solution. The FTIR spectrum of the supernatant solution is shown in FIG. 8 and demonstrates a significant loss of both bridging and terminal CO band intensity. No recarbonylation is observed upon treating this supernatant solution with CO (1.2 atm for 1 hour) as shown in FIG. 8. Dynamic light scattering data in FIG. 9 show the clear presence of large particles after decarbonylation with $Me_3NO$. These particles average in size between 500 nm-600 nm are a result of cluster aggregation.

Alternatively, as discussed above, open clusters can be synthesized comprising a coordinatively unsaturated site comprising a CO vacancy. This vacancy is expected to be a highly active catalyst site, since many reactions depend on highly coordinatively unsaturated sites for catalysis. Such catalysis would include, among others, hydrogenolysis, ammonia synthesis, oxygen dissociation, propylene and acrolein oxidation, CO oxidation, coking, and water-gas shift reactions. Further, in general, the open metal carbonyl clusters of the present invention can be used as catalysts for reducing an organic molecule by contacting the organic molecule with the open metal carbonyl cluster and a reductant. The reducing step can comprise hydrogenation. The organic molecule can be an alkyl hydrocarbon substituted or unsubstituted. The catalytic process can also involve oxidizing an organic molecule by contacting the organic molecule with an open metal carbonyl cluster of the present invention and an oxidant. The oxidation process can comprise hydroxylation.

The open site can be created by reacting the open metal cluster having a CO-labile ligand with a strong acid to remove/coordinate with the CO-labile ligand. For example, triflic acid can be used to remove the ligand trimethylamine from an open metal cluster. The trimethylamine would be coordinated with the triflic acid ($CF_3SO_3H$). Other strong acids can also be used, depending on the CO-labile ligand.

Figure 10:
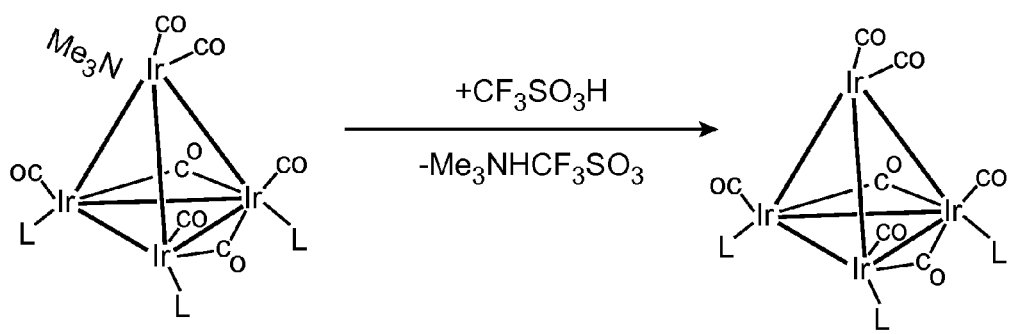
FIG. 10. Schematic illustration of the synthesis of $L_3$ open without amine (right) from $L_3$ open with amine (left). The key involved in this synthesis is the removal of the trimethylamine from the metal carbonyl cluster where it was coordinated to the triflic acid.

The synthesis of such an open cluster, labeled $L_3$ open without amine, is schematically represented in FIG. 10, and can proceed as follows: To a solution of $L_3$ open with amine (51 mg [0.013 mmol] in 3 ml decane), 1 μL of $CF_3SO_3H$ was added. The brown solution turned yellow and a reddish precipitate formed, which is presumed to comprise the [$Me_3NH$][$CF_3SO_3$] salt.

Figure 11:
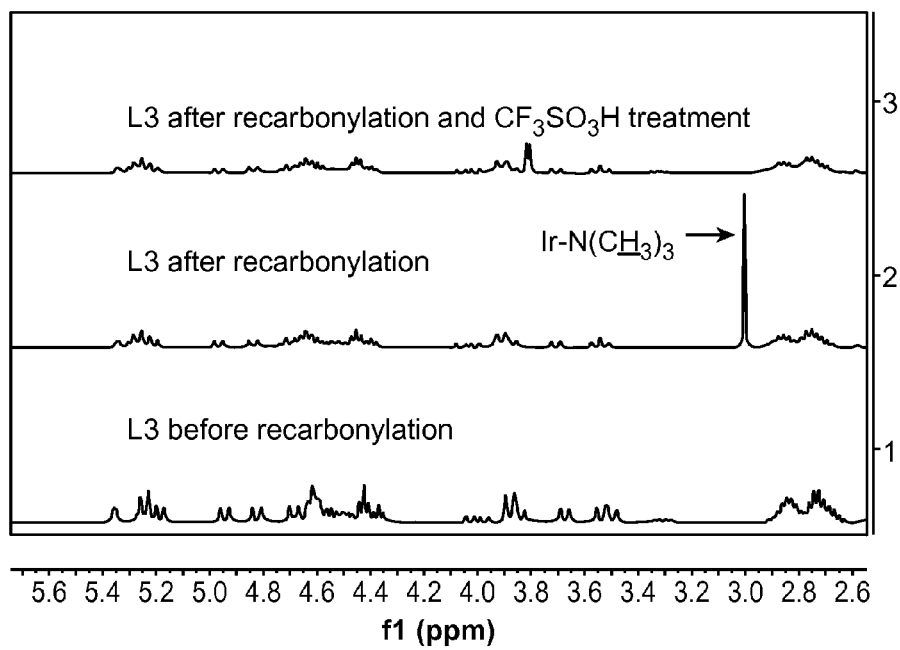
FIG. 11. $^1$H NMR data for $L_3$ closed (bottom), $L_3$ open with amine (middle), and $L_3$ open without amine, corresponding to the cluster shown in the middle after $CF_3SO_3H$ treatment, (top).
Figure 12:
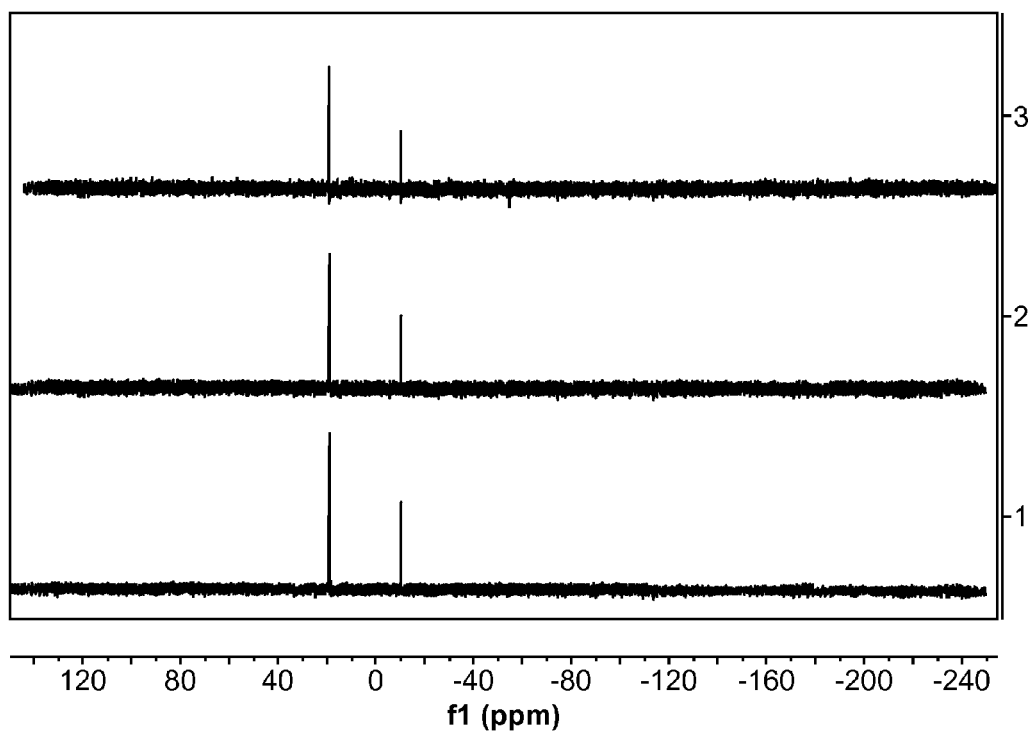
FIG. 12. $^{31}$P NMR data for $L_3$ (bottom), $L_3$ after decarbonylation (middle) and $L_3$ after $CF_3SO_3H$ treatment (top).

The synthesis of a vacant site via disappearance of the resonance representing coordinated trimethylamine can be monitored via $^1H$ NMR spectroscopy in hexane-d14. The $^1H$ NMR spectra before and after $CF_3SO_3H$ addition as recorded in hexane-d14 are shown in FIG. 11. The spectra show that the $Me_3N$ ligand peak at 3 ppm has disappeared after addition of one equivalent of the acid. No further appearance of $[Me_3NH]$ $[CF_3SO_3]$ is observed in the spectrum, which suggests that the precipitate is not soluble in hexane and the solution contains exclusively the yellow $L_3$ open cluster without amine. The $^{31}P$ NMR spectra shown in FIG. 12 demonstrate a lack of phosphine oxidation in all clusters.

Figure 13:
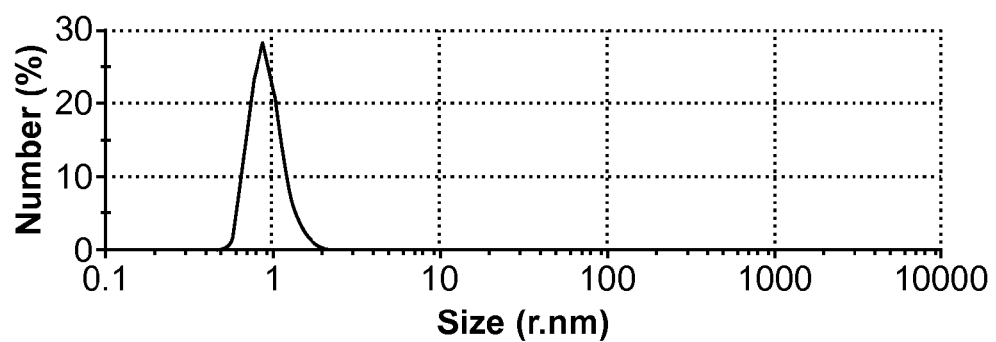
FIG. 13. DLS data of open $L_3$ w/o amine after recarbonylation and $CF_3SO_3H$ treatment FIG. 14. FTIR data of open $L_3$ w/o amine (black), open $L_3$ w/o amine after decarbonylation and $CF_3SO_3H$ treatment (dotted), open $L_3$ w/o amine after recarbonylation (dash-dotted).

The stability of the $L_3$ open without amine cluster was investigated using DLS, following decarbonylation of $L_3$ closed, $CF_3SO_3H$ treatment, and filtration. The data in FIG. 13 show that no aggregation of $Ir_4$ clusters to larger aggregates occurs, as the size of the $L_3$ open without amine cluster matches that measured for $L_3$ closed in FIG. 7. This is presumably the result of the protection afforded by the three bulky calixarene phosphine ligands.

As further evidence of the accessibility and stability of the vacant site in the $L_3$ open without amine cluster, recarbonylation was performed and monitored via FTIR spectroscopy. This was performed by treating a decane solution of $L_3$ open without amine (51 mg (0.013 mmol) in 3 ml decane) with CO gas atmosphere (1.2 atm) for 1 hour. No color change was observed, i.e. solution remained yellow.

Figure 14:
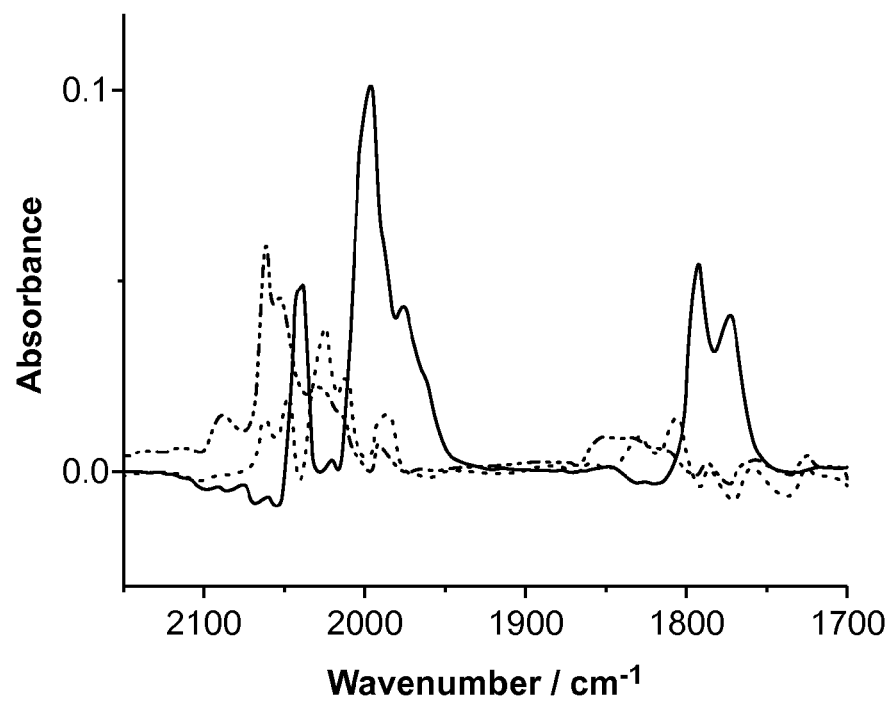

After exposure of $L_3$ open without amine to CO atmosphere, FTIR spectra were recorded and compared to spectra of $L_3$ open without amine prior to recarbonylation. There is a drastic change in the FTIR bands for $L_3$ open without amine following treatment of $L_3$ open with amine with $CF_3SO_3H$ and filtration. This is seen in FIG. 14. The decrease in CO band intensity relative to $L_3$ closed (shown as a solid black line in FIG. 14) is a result of decarbonylation whereas the change of the CO band pattern in the infrared spectrum may indicate a change in the cluster structure. However, a significant increase in CO band intensity is observed after CO exposure of $L_3$ open without amine, during recarbonylation. The recarbonylated spectrum shown in FIG. 14 (dash-dotted line) is unlike the spectrum of $L_3$ closed, further suggesting the synthesis of a different small-sized cluster.

In order to investigate gas-phase processes including catalysis using clusters $L_3$ closed and $L_3$ open with amine, both clusters were separately supported onto an Aerosil-500 silica support consisting of hydroxylated Aerosil silica pretreated to a temperature of 500° C. and stored under inert (water- and air-free conditions). Any suitable conventional catalyst support can be used to support the present open metal clusters. The support can comprise silica, alumina, carbon, magnesium, ceria, or any other support known in the art.

A typical synthesis for supporting such a cluster follows: A solution of either $L_3$ closed or $L_3$ open with amine (51 mg [0.013 mmol] in 3 ml hexane) was added to a suspension of silica (Aerosil 500, 949 mg [15.795 mmol] in 20 ml hexane). The suspension was stirred for 1 hour until the solution became colorless and virtually all cluster compounds were transferred to the silica-solid phase. The solvent was evaporated under vacuum and the resulting powder was dried overnight under vacuum at room temperature. The obtained material contains 1 weight % of iridium are referred to as $L_3$ open with amine @ Aerosil 500 and L3 closed @ Aerosil 500.

Figure 15:
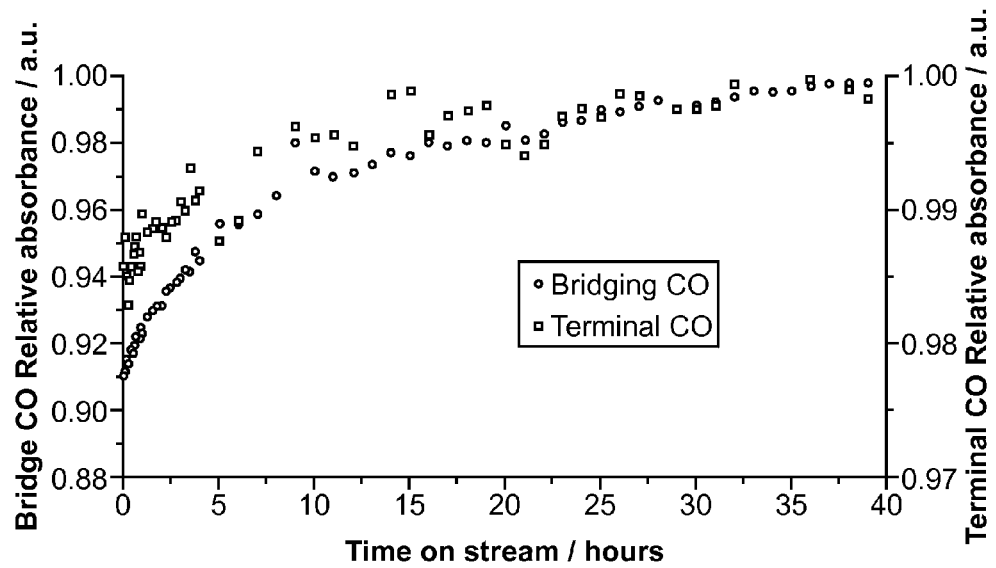
FIG. 15. Intensity versis time during recarbonylation of L3 open with amine @ Aerosil 500 for selected bands corresponding to terminal (1996 $cm^{-1}$) and bridging (1788 $cm^{-1}$) CO bands.

Characterization of $L_3$ open with amine @ Aerosil 500 was first performed by monitoring the changes accompanying recarbonylation via treatment with CO at room temperature. The degree of recarbonylation in the material was quantitatively assessed by monitoring CO bands in the infrared using in-situ FTIR spectroscopy. FTIR spectra after exposure of $L_3$ open with amine @ Aerosil 500 to CO atmosphere are shown in FIG. 15. Following CO treatment, the total integrated intensity for terminal and bridging CO bands increased by 9.0% and 1.4%, respectively. Such an outcome is rather similar to the degree of recarbonylation observed for L3 open with amine in solution (i.e. see FIG. 6). The slightly decreased recarbonylation capacity observed for $L_3$ open with amine @ Aerosil 500 may be due to the presence of the silica surface, which is expected to act as a ligand and partially compete for open coordination sites/sites occupied with CO-labile ligands such as amine. The relatively slow timescale of the recarbonylation observed in FIG. 15, in comparison with the short times represented in FIG. 8, are likely due to mass transport effects through the silica wafer, which is synthesized for the in-situ FTIR measurement (the wafer may have limited porosity and particles inside may take longer to recarbonylate). Notwithstanding these minor differences, the ability to recarbonylate most of the open sites in $L_3$ open with amine @ Aerosil 500 demonstrates that, even when supported on partially dehydroxylated silica, most of the open sites remain available and accessible.

The catalytic activity of $L_3$ open with amine @ Aerosil 500 and of $L_3$ closed @ Aerosil 500 was tested for the ethylene hydrogenation reaction. The reactions were carried out in once-through packed-bed flow reactors at a temperature of 40 C and atmospheric pressure. The packed bed (250 mg of catalyst) was loaded into a u-shaped reactor (with air-free stopcock closures) in an argon-filled glovebox, and installed into the flow system to avoid contacting the catalyst with air. The process lines, and subsequently the packed bed, were purged with He (99.999% purity). The temperature was measured by using a thermocouple placed inside the reactor and immediately upstream of the packed bed. The reactant gases (10 ml/min $H_2$ and 3 ml/min $C_2H_4$) were diluted in a stream of He flowing at 50 ml/min. An online MKS FTIR (Multigas 2030) was used to analyze the reaction products.

Figure 16:
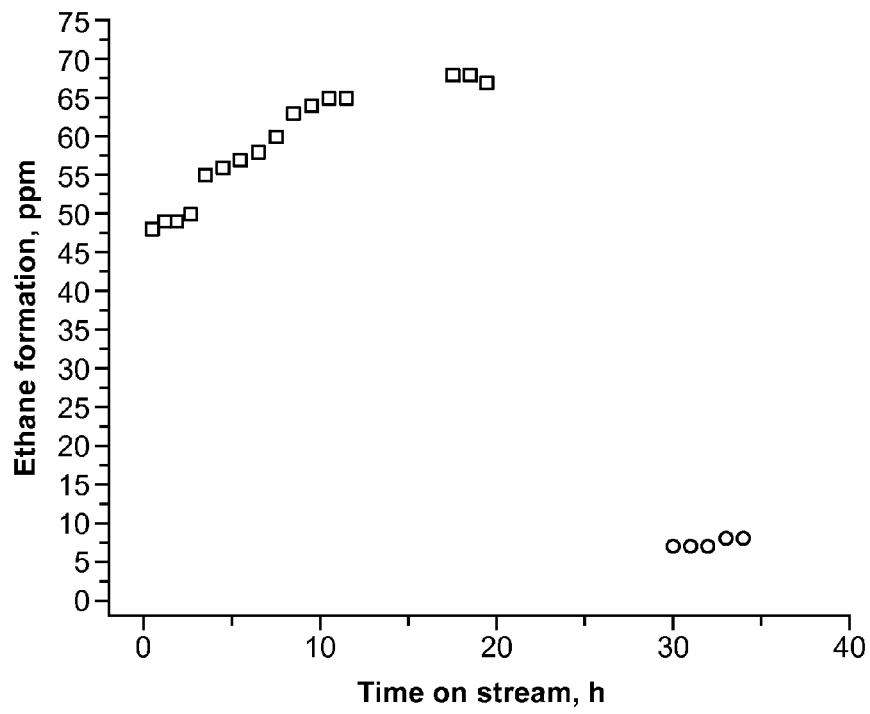
FIG. 16. Formation of ethane (in units of ppm), in the hydrogenation of ethylene by $L_3$ open with amine @ Aerosil 500 (■) and by $L_3$ closed @ Aerosil 500 (●), as a function of time on stream (in units of h) at 40° C. and ambient pressure.

One example of the utility of the $L_3$ open with amine @ Aerosil 500 containing an $Ir_4$ cluster with an easily CO-labile ligand (e.g. amine) is shown in the hydrogenation of ethylene. The formation of ethane was immediately observed (FIG. 16) in the conversion catalyzed by $L_3$ open with amine @ Aerosil 500. The activity increased slightly and was stable for times on stream of more than 12 hours. Formation of ethane in the conversion catalyzed by $L_3$ closed @ Aerosil was only measured at extended times on stream. Ethane formation, shown in Table 1, increased by approximately one order of magnitude from 8 ppm in the conversion catalyzed by $L_3$ closed @ Aerosil 500 to 68 ppm in the conversion catalyzed by the $L_3$ open with amine @ Aerosil 500. The clusters are protected against aggregation on the support and maintain their activity at times on stream greater than 12 hours. These data show that the $L_3$ open with amine @ Aerosil 500, in which the $Ir_4$ contains an easily CO-labile ligand and is sterically protected, results in a more active catalyst for ethylene hydrogenation.

TABLE 1

Steady-state (>12 hour time on stream) formation of ethane in the hydrogenation of ethylene at 40° C.

|  | $L_3$ open with amine @ Aerosil 500 | $L_3$ closed @ Aerosil 500 |
| --- | --- | --- |
| Ethane formation, ppm | 68 | 8 |

Figure 17:
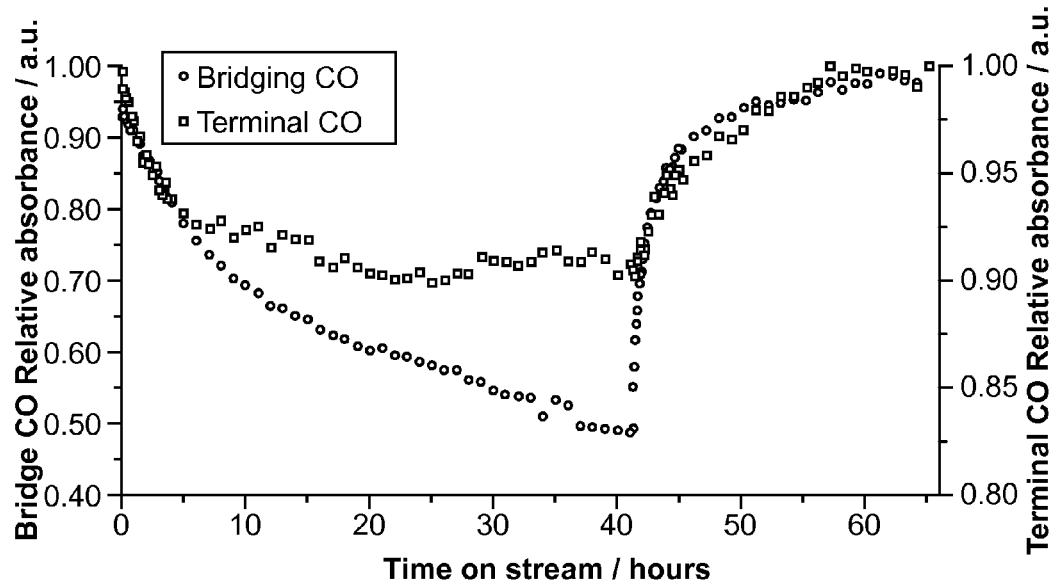
FIG. 17. Integrated intensity for selected peaks corresponding to terminal (1996 $cm^{-1}$) and bridging (1788 $cm^{-1}$) CO bands of $L_3$ open with amine @ Aerosil 500 during ethylene hydrogenation catalysis at 40° C. (from 0 to ~41 hour time on stream) followed by recarbonylation at room temperature (from ~41 hour time on stream onwards).

The stability of catalyst $L_3$ open with amine @ Aerosil 500 under ethylene hydrogenation reaction conditions at 40° C. can also be characterized using in-situ FTIR spectroscopy. As shown in FIG. 17, $L_3$ open with amine @ Aerosil 500 undergoes further decarbonylation during ethylene hydrogenation catalysis at 40° C., as evidenced by the further loss in bridging and terminal band integrated intensity up to ~41 hours time on stream in FIG. 17. The integrated intensity of the terminal and bridging CO bands decreased by 8.3% and 47.5%, respectively, relative to the integrated peak intensities before hydrogenation. Recarbonylation of the used catalyst at room temperature via switching to a CO flow (atmosphere) after ethylene hydrogenation catalysis results in full recarbonylation, to the extent that CO is observed to reoccupy the vacant sites created both during ethylene hydrogenation catalysis as well as during the initial decarbonylation with trimethylamine oxide. The latter point can be clearly observed by the lower initial bridging CO band intensity relative to the final measured one after recarbonylation. Indeed, after recarbonylation, the peak intensities corresponding to terminal and bridging CO bands increased to 7.6% and 1.1%, respectively, relative to the initial values prior to hydrogenation of ethylene. These results are similar to the extent of recarbonylation shown in FIG. 15 above and show that decarbonylation occurring during both treatment with trimethylamine oxide and ethylene hydrogenation catalysis are fully reversible. This in turn strongly suggests a lack of catalyst degradation via aggregation during these processes, since, if such aggregation were occurring, recarbonylation would not be expected to be reversible, as shown in FIG. 17.

Figure 18:
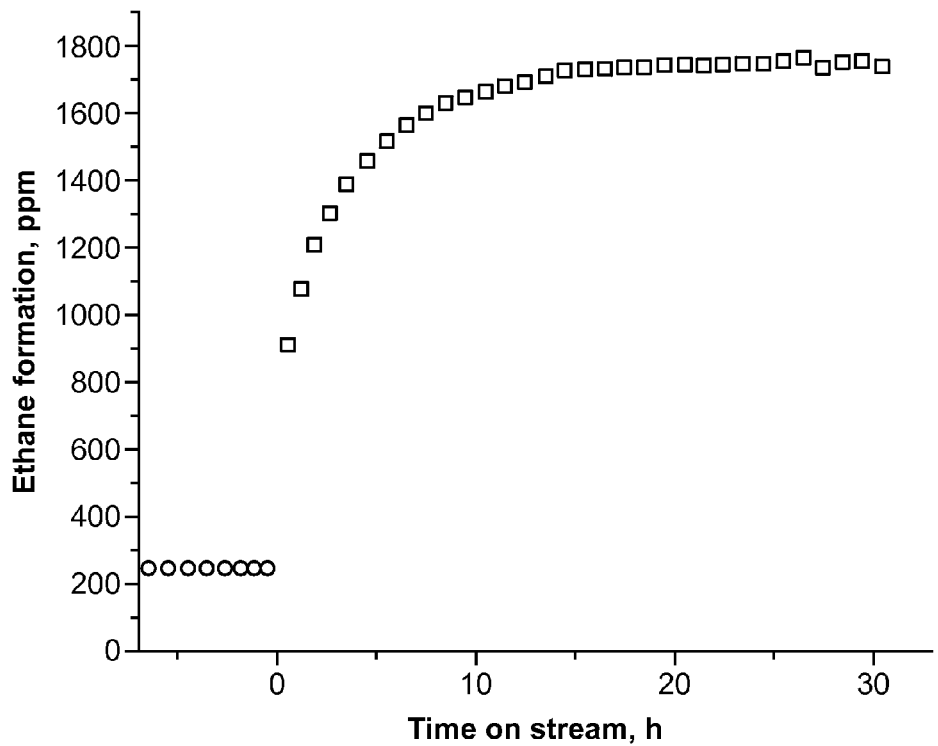
FIG. 18. Formation of ethane (in units of ppm), in the hydrogenation of ethylene by $L_3$ open with amine @ Aerosil 500, BEFORE (●) and AFTER (■) exposure to dry air, as a function of time on stream (in units of h) at 50° C. and ambient pressure.

The catalytic significance of having an open site can also be observed under more forceful conditions in a related catalysis experiment, where pretreatment of the catalyst via oxidation is performed prior to measuring the catalysis rate. This was accomplished by first performing ethylene hydrogenation at 50° C., followed by exposure of the packed bed to a mixture of dry air (Praxair AIO.OXD) flowing at 60 ml/min and He (99.999% purity) flowing at 10 ml/min for 12 hours. The latter procedure completes the catalyst pretreatment. Subsequently, the catalytic activity for ethylene hydrogenation of the pretreated catalyst is measured. The results are shown in FIG. 18 when using $L_3$ open with amine @ Aerosil 500. After the aforementioned pretreatment, the catalyst activity as represented by the ethane formation rate increases to achieve a new maximum at 12 hours time on stream. The catalyst is relatively stable for the subsequent 12-15 hours of time on stream in FIG. 18, though there is slight deactivation observed at longer times on stream. The formation of ethane was increased by nearly one more order of magnitude (Table 2), from 245 to 1766 ppm ethane, when comparing the rate in the first catalytic cycle during the pretreatment procedure versus after pretreatment (and oxygen treatment using dry air). These data show that the $L_3$ open with amine @ Aerosil 500 catalyst, which is sterically protected, can be activated by exposure to oxygen (in this instance via dry air) to create a stable catalyst and active catalyst. Performing a similar pretreatment and catalysis except using $L_3$ closed @ Aerosil 500 results in a 26% lower activity (i.e. 26% lower measured ppm of ethane in the catalyst bed effluent for same number of iridium sites in reactor). Comparing this result with the one shown in Table 2 clearly shows the benefit to having open sites be present, even under forcing pretreatment conditions involving oxygen.

TABLE 2

Steady-state (>12 hour time on stream) formation of ethane in the hydrogenation of ethylene by $L_3$ open with amine @ Aerosil 500 at 50° C. before and after exposure to dry air flowing through the packed-bed reactor

| | Maximum BEFORE exposure to dry air | Maximum AFTER exposure to dry air |
|---|---|---|
| Ethane formation, ppm | 245 | 1766 |

Figure 19:
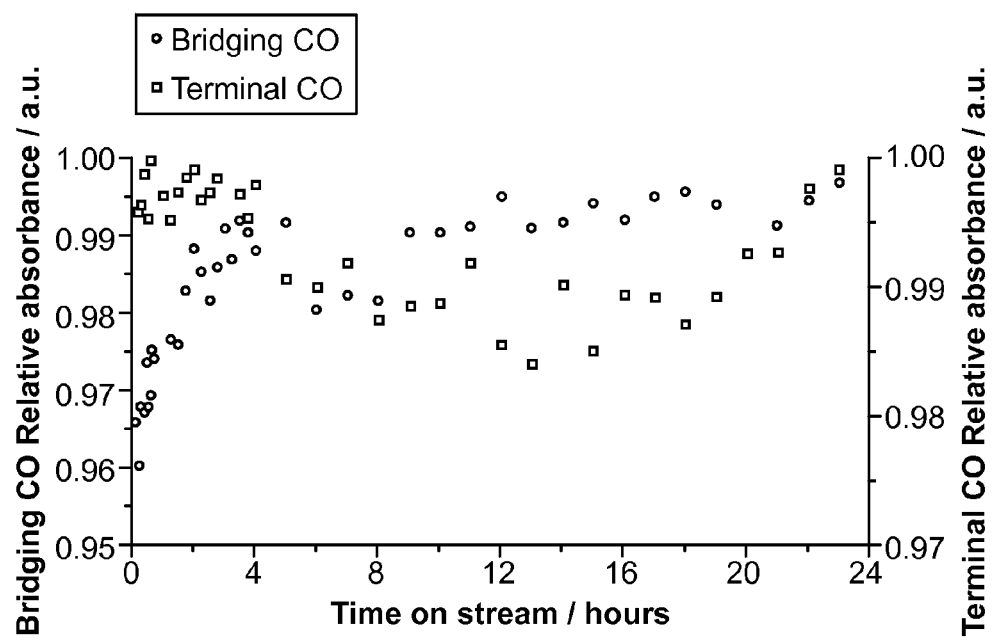
FIG. 19. Intensity versus time during recarbonylation of $L_3$ open without amine @ Aerosil 500 for selected bands corresponding to terminal (1996 $cm^{-1}$) and bridging (1788 $cm^{-1}$) CO bands.

FIG. 19 shows the intensity change of selected carbonyl bands of $L_3$ open without amine @ Aerosil 500 when treated with CO gas. The data show no change for terminal carbonyl ligands and a slight increase of 4% for bridging carbonyl ligands. These data are similar to recarbonylation characteristics that were observed for $L_3$ open without amine in solution (see FIG. 14), and suggests that extensive cluster aggregation does not occur.

The following examples are provided as specific illustrations, and are not meant to be limiting.

Example 1

Synthesis of $Ir_4(CO)_7$[t-butyl-calix[4]arene(OPr)$_3$(OCH$_2$PPh$_2$)]$_3$N(Me)$_3$ (also called $L_3$ open with amine).

A 100 μL of a 0.13 mM solution of Me$_3$NO in dichloromethane (corresponds to 0.13 mmol Me$_3$NO) were added to a solution of $Ir_4(CO)_9$[t-butyl-calix[4]arene(OPr)$_3$(OCH$_2$PPh$_2$)]$_3$ (51 mg, 0.013 mmol, in 3 ml decane). The mixture was stirred for 1 hour. Decarbonylation was accompanied by an immediate change in color of the solution containing the cluster from initial yellow (corresponding to the parent $L_3$ closed cluster in FIG. 2) to brown.

The decarbonylation process is followed using in-situ (time-resolved) FTIR spectroscopy as shown in FIG. 3 for 1787 cm$^{-1}$ (bridging) and 1988 cm$^{-1}$ (terminal). This data shows the decarbonylation to be complete in approximately 10 min, and to result in loss of both terminal and bridging CO ligands. There appears to be a more significant decrease in the bridging versus terminal CO band intensity. This trend is paralleled for data in the integrated CO band intensity for the bridging and terminal regions. The fully integrated CO band intensity drops from 100% to about 93% for terminal CO and to 73% for bridging CO during decarbonylation.

The synthesis of $L_3$ open with amine cluster was also followed via NMR spectroscopy, by performing the decarbonylation as stated above except using deuterated decane-d14 as solvent. FIG. 4 shows the $^1$H NMR spectra both before and after addition of Me$_3$NO. The appearance of a singlet peak at 2.6 ppm with a relative intensity corresponding to ~9H indicates the presence of coordinated Me$_3$N as ligand. $^{31}$P NMR spectra do before and after addition of Me$_3$NO appear unchanged, and, importantly, do not show any evidence of phosphine ligand oxidation (i.e. no phosphine oxide resonances as would be expected in the vicinity of 23 ppm).

Example 2

Synthesis of $Ir_4(CO)_7$[t-butyl-calix[4]arene(OPr)$_3$(OCH$_2$PPh$_2$)]$_3$ (also called $L_3$ open without amine).

The synthesis is schematically represented in FIG. 10, and proceeds as follows. To a solution of $L_3$ open with amine (51 mg (0.013 mmol) in 3 ml decane), 1 μL of CF$_3$SO$_3$H was added. The brown solution turned yellow and a reddish precipitate formed, which is presumed to consist of the [Me$_3$NH][CF$_3$SO$_3$] salt. The synthesis of a vacant site via disappearance of the resonance representing coordinated trimethylamine is monitored via $^1$H NMR spectroscopy in hexane-d14. The $^1$H NMR spectra before and after CF$_3$SO$_3$H addition as recorded in hexane-d14 are shown in FIG. 11. The spectra show that the Me$_3$N ligand peak at 3 ppm has disappeared after addition of one equivalent of the acid. No further appearance of [Me$_3$NH][CF$_3$SO$_3$] is observed in the spectrum, which suggests that the precipitate is not soluble in hexane and the solution contains exclusively the yellow L$_3$ open without amine. The $^{31}$P NMR spectra shown in FIG. 12 demonstrate a lack of phosphine oxidation in all clusters.

Example 3

Synthesis of Ir$_4$(CO)$_7$[t-butyl-calix[4]arene(OPr)$_3$(OCH$_2$PPh$_2$)]$_3$N(Me)$_3$ @ Aerosil 500. Ir$_4$(CO)$_7$[t-butyl-calix[4]arene(OPr)$_3$(OCH$_2$PPh$_2$)]$_3$N(Me)$_3$ (also called as L$_3$ open with amine @ Aerosil 500).

A solution of L$_3$ open with amine (51 mg (0.013 mmol) in 3 ml hexane) was added to a suspension of silica (Aerosil 500, 949 mg (15.795 mmol) in 20 ml hexane). The suspension was stirred for 1 hour until the solution became colorless and virtually all cluster compounds were transferred to the silica-solid phase. The solvent was evaporated under vacuum and the resulting powder was dried overnight under vacuum at room temperature. The obtained material contains 1 weight % of iridium are referred to as L3 open with amine @ Aerosil 500.

Characterization of L$_3$ open with amine @ Aerosil 500 was first performed by monitoring the changes accompanying recarbonylation via treatment with CO at room temperature. The degree of recarbonylation in the material was quantitatively assessed by monitoring CO bands in the infrared using in-situ FTIR spectroscopy. FTIR spectra after exposure of L$_3$ open with amine @ Aerosil 500 to CO atmosphere are shown in FIG. 15. Following CO treatment, the total integrated intensity for terminal and bridging CO bands increased by 9.0% and 1.4%, respectively. Such an outcome is rather similar to the degree of recarbonylation observed for L3 open with amine in solution (i.e. see FIG. 6). The ability to recarbonylate most of the open sites in L$_3$ open with amine @ Aerosil 500 demonstrates that, even when supported on partially dehydroxylated silica, most of the open sites remain available and accessible.

Example 4

Synthesis of Ir$_4$(CO)$_9$[t-butyl-calix[4]arene(OPr)$_3$(OCH$_2$PPh$_2$)]$_3$ @ Aerosil 500 (also called as L3 closed @ Aerosil 500). Ir$_4$(CO)$_9$[t-butyl-calix[4]arene(OPr)$_3$(OCH$_2$PPh$_2$)]$_3$ referred as L$_3$ closed.

A solution of L$_3$ closed (51 mg (0.013 mmol) in 3 ml hexane) was added to a suspension of silica (Aerosil 500, 949 mg (15.795 mmol) in 20 ml hexane). The suspension was stirred for 1 hour until the solution became colorless and virtually all cluster compound was transferred to the silica-solid phase. The solvent was evaporated under vacuum and the resulting powder was dried overnight under vacuum at room temperature. The obtained material contains 1 weight % of iridium are referred to as L3 closed @ Aerosil 500.

Example 5

Catalytic activity of Ir$_4$(CO)$_7$[t-butyl-calix[4]arene(OPr)$_3$(OCH$_2$PPh$_2$)]$_3$N(Me)$_3$ @ Aerosil 500 (L$_3$ open with amine @ Aerosil 500).

Catalytic activity was tested for the ethylene hydrogenation reaction. The reactions were carried out in once-through packed-bed flow reactors at a temperature of 40 C and atmospheric pressure. The packed bed (250 mg of catalyst) was loaded into a u-shaped reactor (with air-free stopcock closures) in an argon-filled glovebox, and installed into the flow system to avoid contacting the catalyst with air. The process lines, and subsequently the packed bed, were purged with He (99.999% purity). The temperature was measured by using a thermocouple placed inside the reactor and immediately upstream of the packed bed. The reactant gases (10 ml/min H$_2$ and 3 ml/min C$_2$H$_4$) were diluted in a stream of He flowing at 50 ml/min. An online MKS FTIR (Multigas 2030) was used to analyze the reaction products.

The formation of ethane was immediately observed (FIG. 16) in the conversion catalyzed by L$_3$ open with amine @ Aerosil 500. The activity increased slightly and was stable for times on stream of more than 12 hour. Steady-state (>12 hour time on stream) formation of ethane in hydrogenation of ethylene at 40 C was 68 ppm.

Example 6

Catalytic activity of Ir$_4$(CO)$_7$[t-butyl-calix[4]arene(OPr)$_3$(OCH$_2$PPh$_2$)]$_3$N(Me)$_3$ @ Aerosil 500 (L$_3$ open with amine @ Aerosil 500).

Catalytic activity was tested for the ethylene hydrogenation reaction, where pretreatment of the catalyst via oxidation is performed prior to measuring the catalysis rate. This was accomplished by first performing ethylene hydrogenation at 50° C., followed by exposure of the packed bed to a mixture of dry air (Praxair AIO.OXD) flowing at 60 ml/min and He (99.999% purity) flowing at 10 ml/min for 12 h. The latter procedure completes the catalyst pretreatment. Subsequently, the catalytic activity for ethylene hydrogenation of the pretreated catalyst is measured. The results are shown in FIG. 18 when using L$_3$ open with amine @ Aerosil 500. After the aforementioned pretreatment, the catalyst activity as represented by the ethane formation rate increases to achieve a new maximum at 12 hour time on stream. The formation of ethane was increased by nearly one more order of magnitude (Table 2), from 245 to 1766 ppm ethane, when comparing the rate in the first catalytic cycle during the pretreatment procedure versus after pretreatment (and oxygen treatment using dry air).

Example 7

In order to verify the stability of the open site on L$_3$ open without amine @ Aerosil 500, recarbonylation via CO treatment was performed and quantitatively assessed via in situ FTIR spectroscopy. FIG. 19 shows the intensity change of selected carbonyl bands of L$_3$ open without amine @ Aerosil 500 when treated with CO gas. The data show no change for terminal carbonyl ligands and a slight increase of 4% for bridging carbonyl ligands. These data are similar to recarbonylation characteristics that were observed for L$_3$ open without amine in solution (see FIG. 14), and suggests that extensive cluster aggregation does not occur.

We claim:
1. A method for preparing an open metal carbonyl cluster comprising chemically reacting a closed metal carbonyl clus- ter and an opening agent, with the opening agent reacting with a bound carbonyl group so as to unbind it from the cluster and leave behind a CO-labile ligand on the cluster, and wherein the closed metal carbonyl cluster is bound with three sterically protective ligands.

2. The method of claim 1, wherein the ligands are calixarene phosphine ligands.

3. The method of claim 1, wherein the closed metal carbonyl cluster is an $Ir_4$ carbonyl cluster bound with three calixarene phosphine ligands, and the opening agent is trimethylamine oxide.

4. The method of claim 1, further comprising recovering the open metal carbonyl cluster, supporting the cluster on a catalyst support, and treating the supported cluster via an oxidation reaction by exposure to oxygen.

5. An open metal carbonyl cluster prepared by the method of claim 1, which is supported on a catalyst support.

6. The open metal carbonyl cluster of claim 5, wherein the catalyst support comprises silica and/or alumina, carbon, magnesia, or ceria.

7. A chemical catalytic reaction comprising conducting a chemical reaction in the presence of the open metal carbonyl cluster prepared in claim 1.

8. A chemical catalytic reaction comprising conducting a chemical reaction in the presence of the supported and treated open metal carbonyl cluster prepared in claim 4.

9. A method for preparing an open metal carbonyl cluster comprising chemically reacting a closed metal carbonyl cluster and an opening agent, with the opening agent reacting with a bound carbonyl group so as to unbind it from the cluster and leave behind a CO-labile ligand on the cluster, and then removing the CO-labile ligand to create vacant sites, wherein the co-labile ligand is removed by reaction with a strong acid or by heating the open metal carbonyl cluster under flow of an inert gas.

10. The method of claim 9, wherein the CO-labile ligand is removed by reaction with a strong acid.

11. The method of claim 10, wherein the strong acid is triflic acid.

12. The method of claim 9, wherein the CO-labile ligand is removed to create vacant sites by heating the open metal carbonyl cluster under flow of an inert gas.

13. The method of claim 9, wherein the CO-labile ligand comprises a trimethylamine oxide ligand.

14. The method of claim 9, wherein the CO-labile ligand is a nitrogen-containing compound coordinating through nitrogen or an oxygen-containing compound coordinating through oxygen.

15. The method of claim 9, wherein the CO-labile ligand is an ether, amine, dioxygen or nitrogen.

16. The method of claim 9, further comprising recovering the open metal carbonyl cluster, supporting the cluster on a catalyst support, and treating the supported cluster via an oxidation reaction by exposure to oxygen.

17. An open metal carbonyl cluster prepared by the method of claim 9, which is supported on a catalyst support.

18. The open metal carbonyl cluster in claim 17, wherein the catalyst support comprises silica and/or alumina, carbon, magnesia, or ceria.

19. A chemical catalytic reaction comprising conducting a chemical reaction in the presence of the open metal carbonyl cluster prepared in claim 9.

20. A chemical catalytic reaction comprising conducting a chemical reaction in the presence of the supported and treated open metal carbonyl cluster prepared in claim 16.

21. The method of claim 9, wherein the closed metal carbonyl cluster is bound with three sterically protective ligands.

22. The method of claim 21, wherein the ligands are calixarene phosphine ligands.

* * * * *